Oct. 20, 1942. F. N. J. KLUG Plant Pat. 553
CARNATION PLANT
Filed April 24, 1942
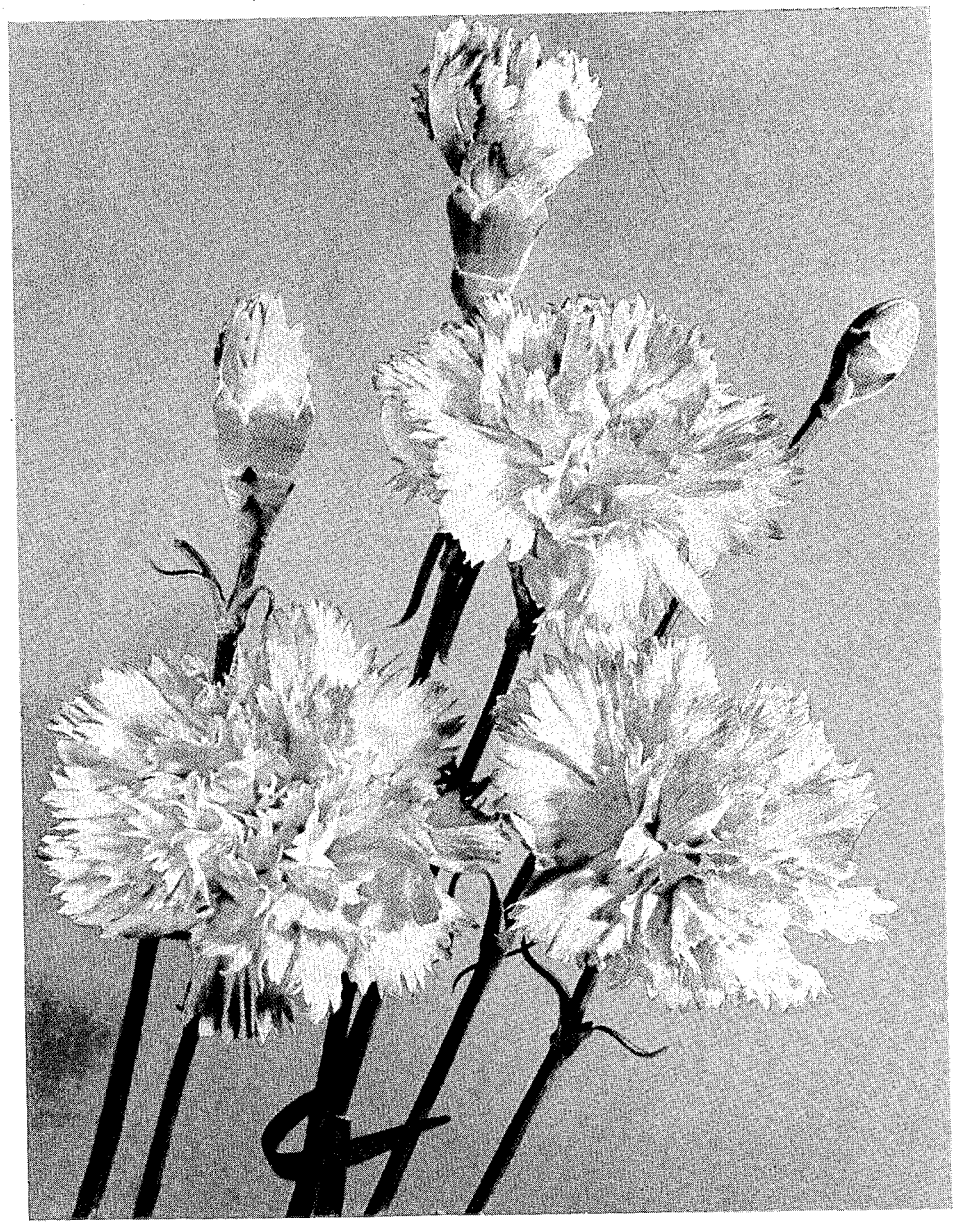
Inventor
F. N. J. Klug
By Robert Cobb
Attorneys Patented Oct. 20, 1942

Plant Pat. 553

UNITED STATES PATENT OFFICE

553

CARNATION PLANT

Fred N. J. Klug, Blue Point, N. Y.

Application April 24, 1942, Serial No. 440,372

1 Claim. (Cl. 47—60)

The present invention relates to a new and distinct variety of carnation plant, originating as a sport found by me on a plant growing in my greenhouses of the variety known to the trade as "Virginia." This latter variety is widely grown and its blossoms are of light pink color.

The present sport of this variety possesses many of the characteristics of its parent, but is distinguished therefrom primarily by the color of the blossoms, namely, the dark pink color, using general color terminology, later given herein in terms of Ridgway's Color Standard for accuracy of identification.

It will be noted from the detail description following that both parent and sport are similarly vigorous growers, heavy producers and disease resistant according to tests with other varieties grown under comparable conditions, and the dark color of said sport represents a highly desirable variation in characteristics of carnations generally, from a commercial standpoint.

The following is a detailed description of this new variety of carnation, the color terminology employed conforming to Ridgway's Color Standard where plate numbers are given; otherwise to general dictionary meaning:

Type: Hardy; tall; greenhouse; sport; for cut flowers.

Breeding or discovery: Sport.

*Parent.*—"Virginia."

Propagations: Holds its distinguishing characteristics through succeeding propagations by cuttings.

*Flower*

Locality where grown: In greenhouses at Blue Point, New York.

Bud:

*Color.*—Deep Rose Pink, Plate XII, splashed with Rose Color, Plate XII, and depths of Rose Color, Plate XII. Base of petal fades to White as it disappears into calyx.

*Peduncle.*—Long; heavy; stiff; numerous in number.

*Flowers borne.*—Singly; on strong, long stems.

*Before calyx breaks.*—*Size*—Medium. *Form*—ovoid; without foliaceous appendages on the surface of the bud, and without foliaceous parts extending beyond the tip of the bud.

*As calyx breaks.*—Light Pink.

*As first petal opens.*—*Size*—Medium. *Form*—ovoid. *Color*—outside and inside, Dark Pink.

*Opening.*—Bud opens up well.

*Calyx.*—Absinthe Green, Plate XXXI, with edges of Deep Olive Buff, Plate XL, and tips of overlapping leaves have a touch of Leaf Green, Plate XLI.

Quantity of bloom: Abundant in greenhouse.

Continuity: Intermittent.

Fragrance: Moderate.

Bloom:

*Size when fully open.*—Large, 3 inches to 3½ inches.

*Petalage.*—Very double (many petals, usually with no stamens showing); from 30 to 40 petals arranged regularly.

*Form.*—Full at first; becoming globular; petals remaining at first tightly rolled inward; becoming later, at maturity, flat.

Petals: Thick; with inside and outside shiny.

*Shape.*—Outside—obovate; scalloped with numerous notches. Intermediate—obovate; scalloped with several notches. Inside—obovate; scalloped with several notches.

*Color.*—Dark Pink.

This description of a newly opened flower was made from a carnation grown in a greenhouse, during the month of February, 1942, at Blue Point, New York:

*Color.*—General petal color Rose Color, Plate XII, with shadows and depths of Tyrian Rose, Plate XII, and Rose Red, Plate XII, giving the flower a brilliant appearance.

This description was made from a carnation that was open for three days in a greenhouse, during the month of February, 1942, at Blue Point, New York:

*Color.*—General petal color Rose Color, Plate XII, with shadows and depths of Tyrian Rose, Plate XII, and Rose Red, Plate XII, giving the flower a brilliant appearance.

*Behavior.*—Persist; not affected by weather.

*Flower longevity.*—Cut flower grown in greenhouse kept at living room temperature, 7 to 10 days after cut.

*Reproductive organs*

Stamens: Very few; arranged regularly.

Filaments: Short to medium; White; few anthers.

Anthers: Small; Yellow.

Pollen: Very sparse.

Pistils: Medium number.

Styles: Even; medium length; medium heavy.

Stigma: White.

Ovaries: Some protruding from calyx.

Sepals: Permanent; moderate length; straight; Green.

Seeds: Normally have none.

*Plant*

Foliage:

*Leaves.*—Normal quantity; medium size; heavy; stiff.

*Color.*—Dusky Yellowish Green, Plate XLI, overlaid with a bloom of Artemisia Green, Plate XLVII.

*Disease.*—Resistant to carnation diseases.

Growth:

*Habit.*—Upright; vigorous.

*Growth.*—Vigorous.

*Stems and leaves.*—Dusky Yellowish Green, Plate XLI, overlaid with a bloom of Artemisia Green, Plate XLVII.

I claim:

A new and distinct variety of carnation plant, characterized as to novelty primarily by the dark color tones in the pink color range, combined with the habit of vigorous growth, productivity, and disease resistance, substantially as shown and described.

FRED N. J. KLUG.